(12) United States Patent
Buis

(10) Patent No.: US 10,849,768 B2
(45) Date of Patent: Dec. 1, 2020

(54) PROSTHESIS CASTING DEVICE

(71) Applicant: University of Strathclyde, Glasgow (GB)

(72) Inventor: Arjan Buis, Glasgow (GB)

(73) Assignee: University of Strathclyde, Glasgow (GB)

( * ) Notice: Subject to any disclaimer, the term of this patent is extended or adjusted under 35 U.S.C. 154(b) by 497 days.

(21) Appl. No.: 15/557,294

(22) PCT Filed: Mar. 11, 2016

(86) PCT No.: PCT/GB2016/050683
§ 371 (c)(1),
(2) Date: Sep. 11, 2017

(87) PCT Pub. No.: WO2016/142718
PCT Pub. Date: Sep. 15, 2016

(65) Prior Publication Data
US 2018/0055662 A1 Mar. 1, 2018

(30) Foreign Application Priority Data
Mar. 11, 2015 (GB) .................................. 1504110.6

(51) Int. Cl.
*A61F 2/80* (2006.01)
*A61F 2/50* (2006.01)
*A61F 2/76* (2006.01)
*A61F 2/78* (2006.01)

(52) U.S. Cl.
CPC .............. *A61F 2/80* (2013.01); *A61F 2/5046* (2013.01); *A61F 2/76* (2013.01); *A61F 2/7812* (2013.01); *A61F 2002/5053* (2013.01); *A61F 2002/5055* (2013.01); *A61F 2002/5083* (2013.01)

(58) Field of Classification Search
CPC .. A51F 2/80; A51F 2/5046; A51F 2/76; A51F 2/7812; A61F 2002/5053; A61F 2002/5055; A61F 2002/5083
USPC ........................................................ 264/222
See application file for complete search history.

(56) References Cited

U.S. PATENT DOCUMENTS

2001/0039159 A1* 11/2001 Janusson ............... A61F 2/5046
442/306

FOREIGN PATENT DOCUMENTS

| WO | WO 1997/017917 A1 | 5/1997 |
|---|---|---|
| WO | WO 1998/018413 A1 | 5/1998 |
| WO | WO 2013/136284 A2 | 9/2013 |

OTHER PUBLICATIONS

International Searching Authority, International Search Report and Written Opinion for International Application No. PCT/GB2016/050683, dated Aug. 23, 2016, 14 pages, European Patent Office, Netherlands.

* cited by examiner

*Primary Examiner* — Jeffrey M Wollschlager
*Assistant Examiner* — Xue H Liu
(74) *Attorney, Agent, or Firm* — Alston & Bird LLP

(57) ABSTRACT

A prosthesis socket casting device having a housing and a flexible membrane for receiving a residual limb, the housing and the membrane defining a cavity for containing a fluid. Within the housing are means that are a function of the patient's weight for altering the distribution of the reactive fluid pressure applied when the residual limb is received within the membrane. In a preferred embodiment, the altering means comprise a movable piston that is provided at a lower end of the housing.

18 Claims, 9 Drawing Sheets

Story Board
The Majicast

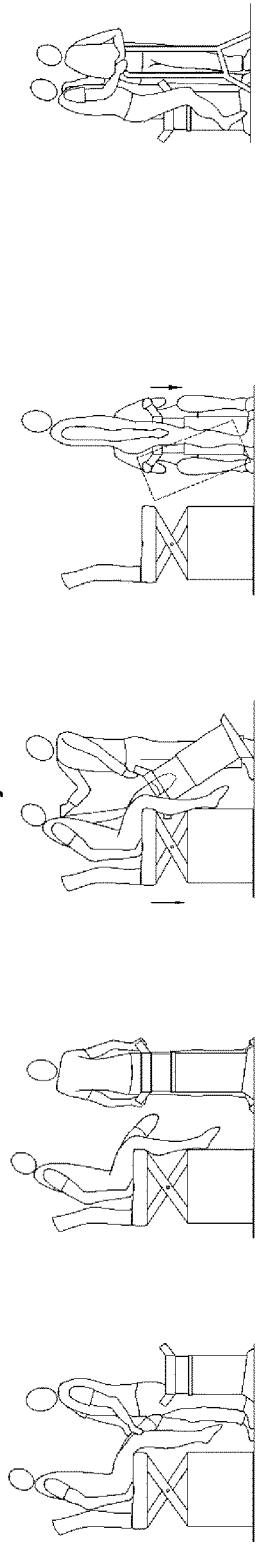

1. Apply plaster
The patient takes a seat and the CPO applies the plaster bandage loosely.

2. Position the Majicast
The patient slides to the end of the seat. The CPO moves the Majicast in position 3. Step into the Majicast
The CPO tips the Majicast and the patient slides into the opening

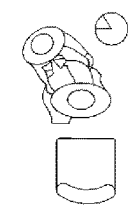

4. The golden point
The CPO lowers the inner tank until it is filled to the top with water, this is known as the "Golden point"

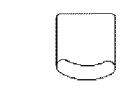

5. Time to apply pressure
The CPO asks the patient to place all the bodyweight onto his residual limb. The pressure buildup in the tank ensures the plaster is formed correctly. A rack aids the patient in keeping his stability

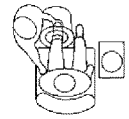

Story Board
The Majicast

6. Put the foot down
The patient can stand on his leg again

7. Tilt the device
The patient is asked to sit down while the CPO slowly tilts the system

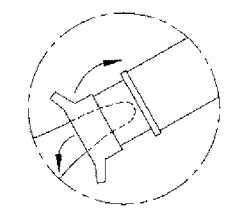

8. Sit and Slide
While the patient sits back the CPO compresses the product

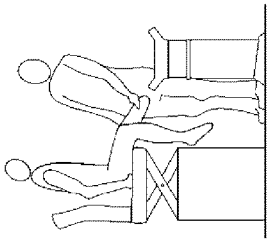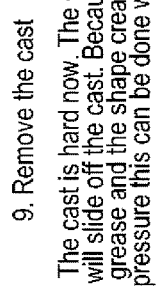

Close up of 8
The counteraction of the movement helps release the lower limb with a stretched knee

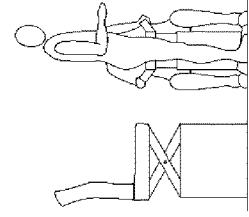

9. Remove the cast
The cast is hard now. The CPO will slide off the cast. Because of the grease and the shape create under pressure this can be done with ease

PROSTHESIS CASTING DEVICE

CROSS REFERENCE TO RELATED APPLICATIONS

This application is a National Stage Application, filed under 35 U.S.C. 371, of International Application No. PCT/GB2016/050683, filed Mar. 11, 2016, which application claims priority to and the benefit of Great Britain Application No. 1504110.6, filed Mar. 11, 2015; the contents of both which as are hereby incorporated by reference in their entirety.

BACKGROUND

Related Field

The present invention relates to a prosthesis-casting device and in particular a casting device for producing a prosthetic socket, for persons with a lower-limb amputation, according the hydrostatic principle.

Description of Related Art

Casting devices used to produce a prosthetic socket according the hydrostatic principle generally have a housing that contains a flexible membrane for receiving a residual limb. Between the housing and the membrane is a loading medium ideally a fluid or gas. In preparation, to form a prosthesis socket, a liner, ideally an elastromeric liner may be donned over the patient's residuum and an uncured or unset casting material is applied. The patient then inserts the residuum with liner and casting material into the flexible membrane and applies their full body weight. This causes the fluid or gas to support the residual limb and conform to its "ideal" shape by exerting a supporting loading condition (pressure) equal and opposite to the patients' applied weight on the casting device. Full body weight is applied until the casting material is set or cured capturing a socket shape under a loaded condition.

In some arrangements, the upward reactive pressure generated during casting can cause some distortion and shortening and widening of the soft tissue at the end of the residuum. To overcome this problem, some prosthesis casting devices include a tensioning mechanism, for example, a spring, which can be used to pull on the residuum to avoid undesired tissue displacement during gait. However, while these systems can be effective, they are manually controlled, which means that there is a risk that excess tensioning may be applied. This can cause the patient pain and discomfort. A further problem with known systems is that after the casting process is completed, it can be difficult for the patient to remove his/her residuum from the casting device.

BRIEF SUMMARY

According to one aspect of the present invention, there is provided a prosthesis socket casting device having a housing, a flexible membrane for receiving a residual limb; a cavity defined between the housing and the membrane for containing a fluid and altering means that are a function of the patient's weight and/or a force applied to the residual limb and/or membrane and/or a pressure of fluid in the cavity for altering the distribution of the reactive fluid pressure applied when the residual limb is received within the membrane.

Preferably, the altering means comprise a piston assembly, which may comprise at least one moveable piston, at a lower end of the housing.

By allowing the piston assembly (which may be attached, e.g. by a cord or similar means, to an elastromeric liner applied to the patient's residuum) to move downwards due to the water pressure induced by the weight of the patient when the patient's stump is in the device, the effective force applied to the end of the stump may be altered, in particular the force may be reduced and the lateral retaining force applied to the sides of the stump may be increased.

The upward force on the distal residuum by the fluid pressure may be reduced by an amount equal to the pressure times the piston area. The application of varying amounts of bodyweight and/or the applied force (that may vary as the patient balances partially on the other foot) may immediately affect a proportionally auto-compensated distal pull by the piston. This reduces distortion at the end of the stump. Because the patient's weight and/or the applied force is used as the input to control the tension, this is a self-setting arrangement that limits or reduces the possibility of excess force being applied to the patient and so decreases the likelihood of pain and discomfort.

The altering means may comprise a braided or woven sleeve or member, which may comprise warp and weft fibres. The braided or woven sleeve or member may comprise or be comprised in a Chinese cuff or trap. The braided or woven sleeve or member may be configured to receive the residual limb. The braided or woven sleeve or member may be comprised, e.g. embedded, in the membrane. The braided or woven sleeve or member may be provided alternately or additionally to the piston assembly.

By providing the braided or woven sleeve or member, e.g. the Chinese cuff or trap, arrangement, as the residual limb is pushed into the braided or woven member, the braided or woven member or sleeve may be stretched longitudinally, thereby reducing the diameter or radial extent of the braided or woven member or sleeve and thereby increasing the lateral retaining force on the sides of the stump.

The flexible membrane may close an opening of the housing. The flexible membrane may be sealed to the housing.

The housing may comprise at least two sections, e.g. at least a first and a second section. The first and second sections may be movable, e.g. slidably movable, relative to each other. The housing may be a telescoping housing. The first and second sections may be telescoping sections, which may telescope relative to each other. The first section may be an upper section. The second section may be a lower section. At least part or all of the first section may be receivable within the second section, e.g. to slidably telescope within the second section.

The piston assembly may be or comprise at least a double piston. The piston arrangement may comprise at least a first piston and a second piston. The first and second pistons may be of different widths. The first piston may be wider than the second piston. The double piston may be formed in a variety of configurations. For example, the membrane may be equivalent to the first piston and the second piston may comprise the movable piston described above. The first (e.g. upper) section of the housing may be equivalent to the first piston of the double piston assembly. Alternatively, a piston assembly comprising a pair of coupled pistons may be provided.

The flexible membrane may be coupled to the first section of the housing. The prosthesis socket casting device may comprise a seal, which may seal between the first and second sections, e.g. between a lower or lowermost part of the first section and an upper or uppermost part of the second section. The seal may preferably be or comprise a rolling membrane, and/or may comprise a sliding membrane, or a pneumatic seal arrangement, and/or an o-ring arrangement. A rolling membrane may reduce friction/drag during movement of the first section relative to the second section. A longitudinal slide mechanism, which may comprise male and female components, may be incorporated between the first section and second section of the housing. The longitudinal slide mechanism may be provided between an inner side surface of the second part of the housing and an outer side surface of the first part of the housing. This may prevent damage to the rolling membrane during operation by only allowing longitudinal movement of the first (e.g. upper) section relative to the second (e.g. lower) section, and by preventing rotational movement of the first section relative to the second section.

The cavity may be a two part cavity, which may comprise at least a first cavity section and a second cavity section. The first section of the housing may define at least the first cavity section, e.g. within the first section of the housing. In other words, the first cavity section may be at least partially defined by an inner surface of the first housing section and optionally also by the membrane.

The second cavity section may be at least partially defined by one or more or each of: an outer surface of the first section of the housing, an inner surface of the second cavity section and/or the seal. At least one port or opening may be provided between the first cavity section and the second cavity section, e.g. to allow fluid communication therethrough. The at least one port or opening may be provided through a wall and/or base of the first section of the housing.

The prosthesis socket casting device may be configured such that the housing is extendable, e.g. by extending, moving, sliding or telescoping the first (e.g. upper) section such that it is at least partially or fully extended out or away from second (e.g. lower) section. Extending the housing may put the prosthesis socket casting device in an open, e.g. initial or pre-use, configuration. The housing may be extendable by moving or pulling at least part of the first (e.g. upper) section away from or relative to the second section. The first (e.g. upper) section may comprise handles for moving or pulling at least part of the first section away from or relative to the second section. The handles may be ergonomically designed handles.

The cavity between the housing and the flexible membrane may be a sealed cavity. The cavity (e.g. both the first and second cavity sections) may be filled with an uncompressible fluid, preferably water.

With the above arrangement, when the housing is extended, e.g. such that the first section is at least partially or fully extended out of or away from the second section, for example by pulling the first and/or second sections of the housing, e.g. in opposing directions, the flexible membrane may be caused to expand towards the inner surface/walls of the first section of the housing, as the volume of the second cavity section increases. In other words, by extending the housing so as to increase the volume of the second cavity section, since the first and second cavity sections are in fluid communication via the ports through the first section of the housing, the pressure in the first cavity section reduces. This causes a differential in pressure between the air pressure on an outer surface of the membrane and the fluid pressure on an inner surface of the membrane that faces into the first cavity section. This pressure differential causes the membrane to move towards the inner surface/walls of the first section of the housing, thereby reducing the volume of the first cavity section and equalising the pressure differential. This may result in the open configuration, which may be the initial or pre-use configuration, for insertion and/or removal of the residual limb. The open configuration, which may be the initial or pre-use configuration, may also result in the piston (e.g. the second piston) being selectively moved to and/or locked in a first or initial position. The piston (e.g. the second piston) may be selectively moved to and/or locked in a first or initial position by a force, e.g. applied by or resulting from the flexible membrane as the flexible membrane is caused to expand towards the inner surface/walls of the first section of the housing when the housing is extended, which may be such that the first section is at least partially or fully extended out of or away from the second section, for example by pulling the first and/or second sections of the housing, e.g. in opposing directions.

When the prosthesis socket casting device is in the open configuration, a patient's residual limb may be pushed into the expanded flexible membrane. Since the membrane has been forced out towards the inner surface of the first section of the housing, a relatively large receiving volume is defined by the outer surface of the membrane into which the residual limb may be easily inserted and/or removed.

The prosthesis casting device may be configured to at least partially contract the housing, e.g. by pushing the first (e.g. upper) section of the housing into the second (e.g. lower) section of the housing, e.g. by the force of inserting the residual limb and/or the weight of the patient. This may result in the pressure of the fluid in the cavity pushing the flexible membrane against the residual limb as the volume of the second cavity section in the second (e.g. lower) section of the housing decreases and fluid is forced from the second cavity section into the first cavity section via the ports in the first section of the housing. The position of the flexible membrane relative to the walls of the upper section of the housing may be a function of the position of the upper section of the housing relative to the position of the lower section of the housing. In this way it may be possible for the prosthesis socket casting device to be self-contained or stand-alone, without the need for any separate device to pressurise the fluid in the cavity. It may be a hands-off device, which may be portable, easy to use, and provide repetitive and consistent results. Furthermore, the above configuration may improve the ease of insertion and/or removal of the residual limb. In addition, a range of residual limb sizes may be more easily accommodated.

In this way, the at least two part housing may be considered to at least partially provide the altering means for altering the distribution of the reactive fluid pressure applied when the residual limb is received within the membrane.

It will be appreciated that a plurality of altering means for altering the distribution of the reactive fluid pressure applied when the residual limb is received within the membrane may be provided. For example, the prosthesis socket casting device may comprise one or more or each of the piston assembly, the braided or woven member or sleeve and/or the at least two part or telescoping housing, or any combination thereof.

For example, at least part or all of the piston assembly, e.g. the second piston, may be comprised in a wall or surface of the housing, which may be the first section of the housing, e.g. in a base of the first section of the housing. At least one surface of at least the part of the piston assembly (e.g. the second piston) may be configured to be exposed to the fluid in the first cavity section, e.g. by facing into the first section of the housing.

At least the part of the piston assembly (e.g. the second piston) may be selectively or releasably coupled or couplable with the first section of the housing. The prosthesis socket casting device may be configured such that the piston (e.g. the second piston) of the piston assembly is selectively coupled to the housing, e.g. to the first section of the housing, such that there is no relative movement between the piston (e.g. the second piston) and the housing or the first section of the housing when a differential pressure on the piston is less than a threshold amount. The prosthesis socket casting device may be configured such that the piston (e.g. the second piston) is selectively released from the housing, e.g. from the first section of the housing, such that the piston (e.g. the second piston) is movable relative to the housing or the first section of the housing when a differential pressure on the piston (e.g. the second piston) is greater than a threshold amount. For example the piston (e.g. the second piston) may be press fit into a passage or cylinder provided in or coupled to the housing, e.g. to the first section of the housing such as to the base of the first section of the housing.

In this way, the prosthesis socket casting device may be configured to provide at least a two stage action, namely at least a first stage where the first and second sections of the housing are movable relative to each other in order to increase and reduce the size of a recess defined by the membrane to allow easy insertion and/or removal of the residual limb and to provide an initial lateral force on the residual limb when inserted. When the pressure in the first cavity section increases, a pressure differential on the piston (e.g. the second piston) may increase beyond the threshold. In this case, the piston (e.g. the second piston) may move, which may apply a force on the elastromeric liner to which it is connected, which may in turn apply a lateral pressure on the residual limb and may increase the distal pull on the residual limb. This may control the shape at the end of the residual limb.

The size of the piston (e.g. of the first and/or second pistons) may be suitably chosen so that a clinically correct adjustment can be effected. In practice, a table of weights, patient measures and preferred piston diameters would be provided.

In an embodiment in which the piston assembly comprises at least a double piston, one side of the first piston may be in contact with the fluid of the cavity of the prosthesis socket casting device.

The opposing side of the first piston may be in contact with a fluid which is in contact with one side of the second piston. The chamber of the first piston and the chamber of the second piston may be a single volume filled with fluid. The fluid in contact with both the first and second pistons may be uncompressible, preferably water. The first and second pistons may be connected, coupled, or preferably tethered together. The tether may initially be unstrained, or slack, between the first and second pistons. Linear movement of the first wider piston in response to the patient's weight may result in greater linear movement of the second narrower piston due to the movement of the uncompressible fluid. These different rates of linear movement of the first and second pistons may result in the tether connecting the first and second pistons becoming strained. This strain in the tether may prevent further linear movement of the first piston, which may result in an increase in the pressure of the fluid in the cavity. The minimum strain in the tether may be approximately 2.5 kg, or 25 Newtons. This strain acts on the soft tissue of the patient's residual limb to remove slack from the soft tissue. Removing the slack from the soft tissue allows load to be more efficiently carried from the resulting prosthetic to the bone of the patient's residual limb.

The dimensions of the piston (e.g. of the first and/or second piston) may vary with the material properties of the liner. The width of the piston, and/or the widths of the first and second pistons, may be functions of the material of the liner, the thickness of the liner, the length of the liner, the elasticity of the liner, or the like.

The piston (e.g. the second piston) may be selectively locked or lockable in a first or initial position. The piston may be selectively unlocked and allowed to move, e.g. once sufficient force is applied, preferably greater than a threshold force. This force may be applied by the patient's weight, such that the piston cannot move when the patient's residual limb is first placed in the flexible membrane, but the piston may move once the patient's weight is applied through the patient's residual limb to the flexible membrane.

According to another aspect of the invention there is provided a prosthesis socket casting device that is collapsible.

Providing a collapsible casting device, makes it is significantly easier for a patient to remove their residuum at the end of the casting process. Also, collapsing the device allows it to be portable.

The device may have a collapsible external housing. The preferred means of collapsibility is through telescopic means, but equally well through the use of a foldable but non-stretch external housing, or as another implementation a concertina construction.

According to another aspect of the invention there is provided a prosthesis socket casting device to produce a prosthetic socket according to the hydrostatic principle comprising a rigid or collapsible housing, a membrane within the housing for receiving a patient's residual limb and a diaphragm having a variable size aperture at an upper end of the housing.

By using a variable sized aperture diaphragm at the upper end of the housing, there is provided a very simple mechanism for closing the casting device, regardless of the size or diameter of the patient's residuum.

Providing a close fit to the patients' limb is desirable to prevent a thin inner membrane from being damaged by the internal fluid pressure that would balloon this membrane out of the device through the gap between the external housing and the residual limb at the level of entry onto the device. The use of a variable sized aperture diaphragm allows such a close fit, which in turn allows a thinner and/or more flexible membrane to be used to cast the pressurised shape of the residual distal limb. In practice, the thinner the membrane, the more ideal pressure distribution can be achieved.

The diaphragm may comprise a braided material or weave, which may be configured such that the diaphragm constricts around a patient's residual limb when the limb is pushed through the aperture in the diaphragm. The weave of the diaphragm may be or comprise a Chinese cuff or trap, or similar. The diaphragm may form the top of the flexible membrane.

According to still another aspect of the invention there is provided a prosthesis socket casting device comprising a housing, a flexible membrane for receiving a residual limb; a cavity defined between the housing and the membrane for containing a fluid and an input fluid pressuriser. The pressuriser is provided for volume compensation of the fluid as it is being input to the cavity, so that the device can be quickly filled and the patient rapidly can apply their weight.

By pressurising the fluid as it is being input to the cavity, quick adjustments in the fluid volume can be made. Because time is of a premium in the casting process, this assists in minimising distortions and loss of high quality shape capture through interference or partial cure of the casting material.

According to still another aspect of the invention there is provided a prosthesis socket casting device comprising a housing, a flexible membrane for receiving a residual limb; and a cavity defined between the housing and the membrane for containing a fluid. The housing may have a variable volume. The housing may be or comprise a telescoping housing. The flexible membrane may be movable responsive to the telescoping of the housing and/or variations in the volume of the housing.

The flexible membrane may close an opening of the housing. The flexible membrane may be sealed to the housing.

The housing may comprise at least two sections, e.g. at least a first and a second section. The first and second sections may be movable, e.g. slidably movable, relative to each other. The first and second sections may be telescoping sections, which may telescope relative to each other. The first section may be an upper section. The second section may be a lower section. At least part or all of the first section may be receivable within the second section, e.g. to slidably telescope within the second section.

The flexible membrane may be coupled to the first section of the housing. The prosthesis socket casting device may comprise a seal, which may seal between the first and second sections, e.g. between a lower or lowermost part of the first section and an upper or uppermost part of the second section. The seal may preferably be or comprise a rolling membrane, and/or may comprise a sliding membrane, or a pneumatic seal arrangement, and/or an o-ring arrangement. A rolling membrane may reduce friction/drag during movement of the first section relative to the second section. A longitudinal slide mechanism, which may comprise male and female components, may be incorporated between the first section and second section of the housing. The longitudinal slide mechanism may be provided between an inner side surface of the second part of the housing and an outer side surface of the first part of the housing. This may prevent damage to the rolling membrane during operation by only allowing longitudinal movement of the first (e.g. upper) section relative to the second (e.g. lower) section, and by preventing rotational movement of the first section relative to the second section.

The cavity may be a two part cavity, which may comprise at least a first cavity section and a second cavity section. The first section of the housing may define at least the first cavity section, e.g. within the first section of the housing. In other words, the first cavity section may be at least partially defined by an inner surface of the first housing section and optionally also by the membrane.

The second cavity section may be at least partially defined by one or more or each of: an outer surface of the first section of the housing, an inner surface of the second cavity section and/or the seal. At least one port or opening may be provided between the first cavity section and the second cavity section, e.g. to allow fluid communication therethrough. The at least one port or opening may be provided through a wall and/or base of the first piston section.

The prosthesis socket casting device may be configured such that pulling the first (e.g. upper) section such that extending the housing, e.g. extending the first (e.g. upper) section such that it is at least partially or fully extended out or away from second (e.g. lower) section, may put the prosthesis socket casting device in an initial or pre-use configuration. The first (e.g. upper) section may comprise handles for pulling the first section away from the second section. The handles may be ergonomically designed handles.

The cavity between the housing and the flexible membrane may be a sealed cavity. The cavity (e.g. both the first and second cavity sections) may be filled with an uncompressible fluid, preferably water.

With the above arrangement, when the housing is extended, e.g. such that the first section is at least partially or fully extended out of or away from the second section, for example by pulling the first and/or second sections of the housing, e.g. in opposing directions, the flexible membrane may be caused to expand towards the inner surface/walls of the first section of the housing, as the volume of the second cavity section increases. In other words, by extending the housing so as to increase the volume of the second cavity section, since the first and second cavity sections are in fluid communication via the ports through the first section of the housing, the pressure in the first cavity section reduces. This causes a differential in pressure between the air pressure on an outer surface of the membrane and the fluid pressure on an inner surface of the membrane that faces into the first cavity section. This pressure differential causes the membrane to move towards the inner surface/walls of the first section of the housing, thereby reducing the volume of the first cavity section and equalising the pressure differential. This may result in an open configuration, which may be an initial or pre-use configuration, for insertion and/or removal of the residual limb.

When the prosthesis socket casting device is in the open configuration, a patient's residual limb may be pushed into the expanded flexible membrane. Since the membrane has been forced out towards the inner surface of the first section of the housing, a relatively large receiving volume or recess is defined by the outer surface of the membrane into which the residual limb may be easily inserted and/or removed.

The prosthesis casting device may be configured such that the force of inserting the residual limb and/or the weight of the patient may at least partially contract the housing, e.g. by pushing the first (e.g. upper) section of the housing into the second (e.g. lower) section of the housing. This may result in the pressure of the fluid in the cavity pushing the flexible membrane against the residual limb as the volume of the second cavity section in the second (e.g. lower) section of the housing decreases and fluid is forced from the second cavity section into the first cavity section via the ports in the first section of the housing. The position of the flexible membrane relative to the walls of the upper section of the housing may be a function of the position of the upper section of the housing relative to the position of the lower section of the housing. In this way it may be possible for the prosthesis socket casting device to be self-contained or stand-alone, without the need for any separate device to pressurise the fluid in the cavity. It may be a hands-off device, which may be portable, easy to use, and provide repetitive and consistent results.

At least part or all of a piston assembly, which may comprise a piston slidably mounted within a passage, may be comprised in a wall or surface of the housing, which may be the first section of the housing, e.g. in a base of the first section of the housing. At least one surface of at least the part of the piston assembly (e.g. the piston) may be configured to be exposed to the fluid in the first cavity section, e.g. by facing into the first section of the housing.

At least the part of the piston assembly (e.g. the piston) may be selectively or releasably coupled or couplable with the first section of the housing. The prosthesis socket casting device may be configured such that the piston of the piston assembly is selectively coupled to the housing, e.g. to the first section of the housing, such that there is no relative movement between the piston and the housing or the first section of the housing when a differential pressure on the piston is less than a threshold amount. The a prosthesis socket casting device may be configured such that the piston is selectively released from the housing, e.g. from the first section of the housing, such that the piston is movable relative to the housing or the first section of the housing when a differential pressure on the piston is greater than a threshold amount. For example the piston may be press fit into a passage or cylinder provided or coupled to the housing, e.g. to the first section of the housing such as to the base of the first section of the housing. The release force for releasing the press fit may be equivalent to the force applied by the threshold pressure differential.

In this way, the prosthesis socket casting device may be configured to provide at least a two stage action, namely at least a first stage where the first and second sections of the housing are movable relative to each other in order to increase and reduce the size of an opening defined by the membrane to allow easy insertion and/or removal of the residual limb and to provide an initial lateral force on the residual limb when inserted. When the pressure in the first cavity section increases, a pressure differential on the piston may increase beyond the threshold. This may cause the piston to move, which may apply a force on the elastromeric liner to which it is connected, which may in turn apply a lateral pressure on the residual limb and may increase the distal pull on the residual limb. This may control the shape at the end of the residual limb.

According to still another aspect of the invention there is provided a liner, which may be for use with, and/or for use as the flexible membrane of, the prosthesis socket casting device according to any of the previous aspects of the invention, wherein the liner comprises a braided material or weave, which may be configured such that the liner constricts around the patient's residual limb when force or pressure is applied along the limb and through the liner, e.g. in a longitudinal direction of the limb and/or liner. This force or pressure may be due to some or all of the patient's weight. The weave may be or form a Chinese cuff or trap weave, or similar. The Chinese cuff or trap may be incorporated or embedded into the liner. For example, the braided material or weave may be embedded in a matrix such as an impermeable matrix of flexible material, such as a polymeric material. Walls, e.g. side walls, of the liner may vary in thickness or comprise a thickness gradient, which may vary in a longitudinal direction of the liner. The liner may be thicker at a top end, or thicker at an end furthest from the end of the patient's residual limb. The Chinese cuff may extend over the whole length of the liner, or partially along a length of a liner, preferably from a thicker portion of the liner to the other end of the liner. The Chinese cuff may be coupled to an opening of the housing. The liner may be formed from a natural fibre composite.

According to an aspect of the invention is a method of forming a cast of a residual limb. The method may comprise using a prosthesis socket casting device according or described in relation to any of the preceding aspects and/or a liner according or described in relation to any of the preceding aspects. The method may comprise inserting a residual limb into an elastomeric liner. The elastomeric liner may be connected to a piston (e.g. a first or second piston) of the prosthesis socket casting device. The method may comprise providing a casting material, e.g. onto a membrane of the prosthesis socket casting device and/or into a cavity formed by the membrane of the prosthesis socket casting device.

The method may comprise expanding or extending a housing of the prosthesis socket casting device, e.g. by moving, sliding or telescoping at least part or all of at least part of a first section of the housing relative to, out of, and/or away from at least part of a second section of the housing. The method may comprise moving the membrane towards an inner surface of at least a first section of the housing by reducing the pressure in a first cavity section in the first section of the housing. The method may comprise moving the membrane radially outwardly and/or towards an inner surface of at least a first section of the housing, e.g. by the relative moving, sliding or telescoping of the first and second sections of the housing.

The method may comprise inserting the residual limb into a recess formed by the membrane, e.g. after the membrane has been moved radially outwardly and/or towards an inner surface of the first section of the housing. The method may comprise forcing and/or moving at least part or all of the membrane radially inwardly and/or towards and/or into contact with the residual limb, e.g. after it has been inserted into the recess. The method may comprise contracting or retracting the housing, e.g. by moving, sliding or telescoping at least part or all of at least the first section of the housing relative to, into or towards at least part of the second section of the housing. The method may comprise moving the membrane radially inwardly and/or towards an inner surface of at least a first section of the housing by increasing the pressure in a first cavity section in the first section of the housing. The method may comprise moving or forcing the membrane towards or onto the residual limb, e.g. by the relative moving, sliding or telescoping of the first and second sections of the housing.

The method may comprise further contracting or retracting the housing by placing further weight or force on the residual limb. The method may comprise causing the piston (e.g. the second piston) to operate or move by causing a pressure differential greater than a threshold amount on the piston.

It should be understood that the features defined above in accordance with any aspect or below in relation to any specific embodiment may be utilised, either alone or in combination with any other defined feature, in any other aspect or embodiment. Furthermore, the present invention is intended to cover apparatus configured to perform any feature described herein in relation to a method and/or a method of using, installing, producing or manufacturing any apparatus feature described herein.

BRIEF DESCRIPTION OF THE FIGURES

Various aspects of the invention will now be described by way of example only and with reference to the following drawings, of which:

FIG. 10 (d) is a negative mould made from plaster of a patient's limb made using a prosthesis socket casting device, and a negative mould made from a glass fibre bandage material of a patient's limb made using a prosthesis socket casting device;

FIGS. 10 (e) and (f) are a prosthesis socket casting device;

FIG. 10 (g) is a method of using a prosthesis socket casting device; and

DETAILED DESCRIPTION OF VARIOUS EMBODIMENTS

Figure 1:
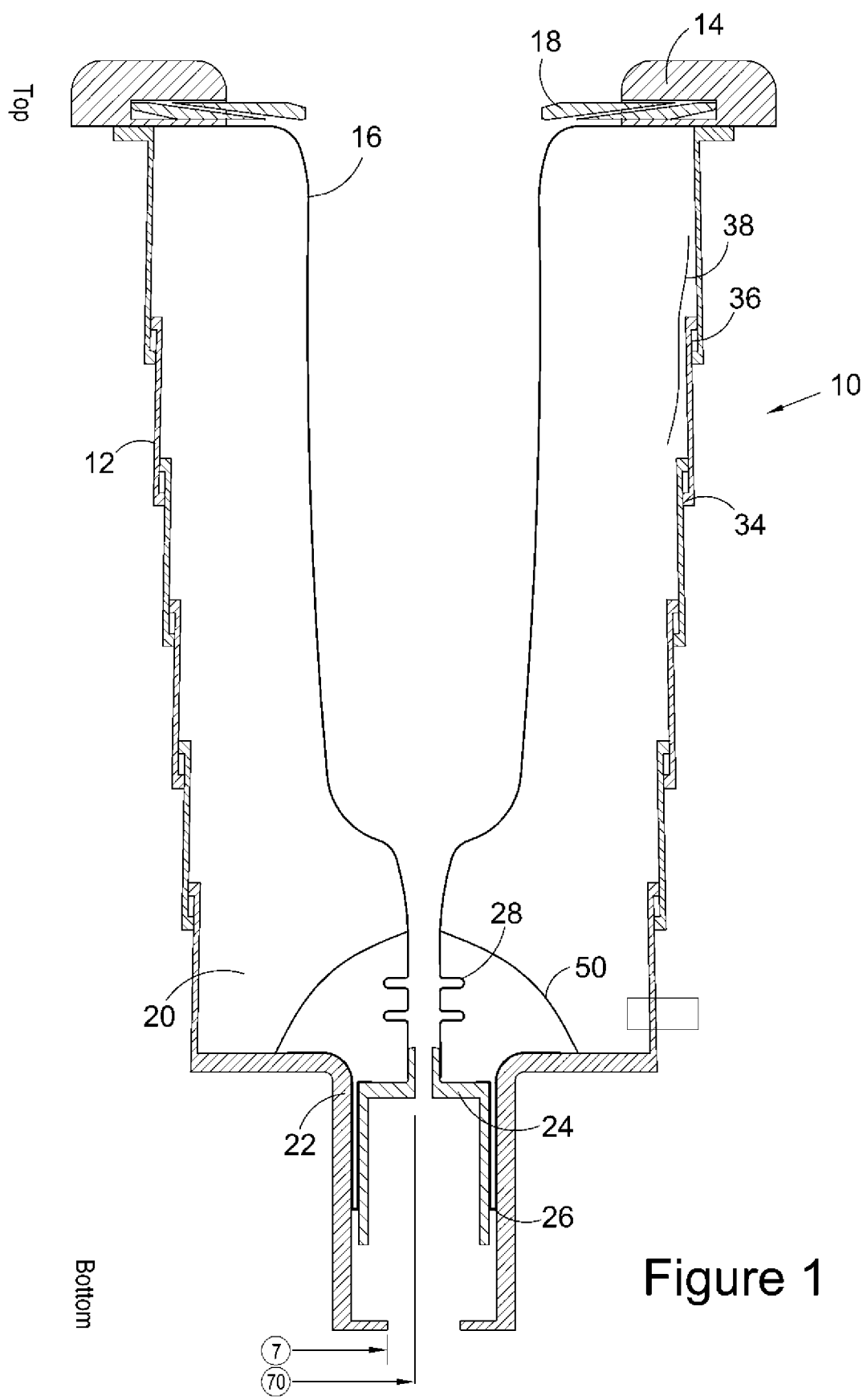
FIG. 1 is a cross-section through a prosthesis socket casting device.

FIG. 1 shows a prosthesis casting device 10 that has a rigid external housing 12. At a top end of the housing 12 is an annular rim 14, attached to which is one end of a flexible membrane 16 that is adapted to receive a patient's residuum. Also at the top end of the housing 12 is a variable aperture diaphragm 18 that can be moved into contact with a patient's residuum in use, thereby to close the end of the housing 12.

Between the flexible membrane 16 and the housing 12 is a cavity 20 for receiving a loading medium, ideally a fluid or gas, but most conveniently water. Fluid can be introduced into the cavity as and when desired using any suitable valve (not shown). Opening into a lower end of the housing 16 is a lower cup 22 within which is a moveable piston 24. A limiting mechanism (not shown) is provided to limit the downward piston movement. Between the piston 24 and the housing 16 is a rolling membrane 26 that extends fully around the periphery of the piston 24 and allows it to move whilst simultaneously providing a seal to prevent leakage of water from the cavity 20. On an upper end of the piston 24 is a protrusion 26 to which a lower end of the flexible membrane 16 is attached. To accommodate movement of the piston without overly distorting the main body of the membrane 16, a narrow corrugated section 28 is provided at the membrane's lower end. This assists in lowering the longitudinal modulus of elasticity of the membrane. Other corrugations may be included in the membrane design to further lower the modulus of elasticity in the various directions.

Figure 2:
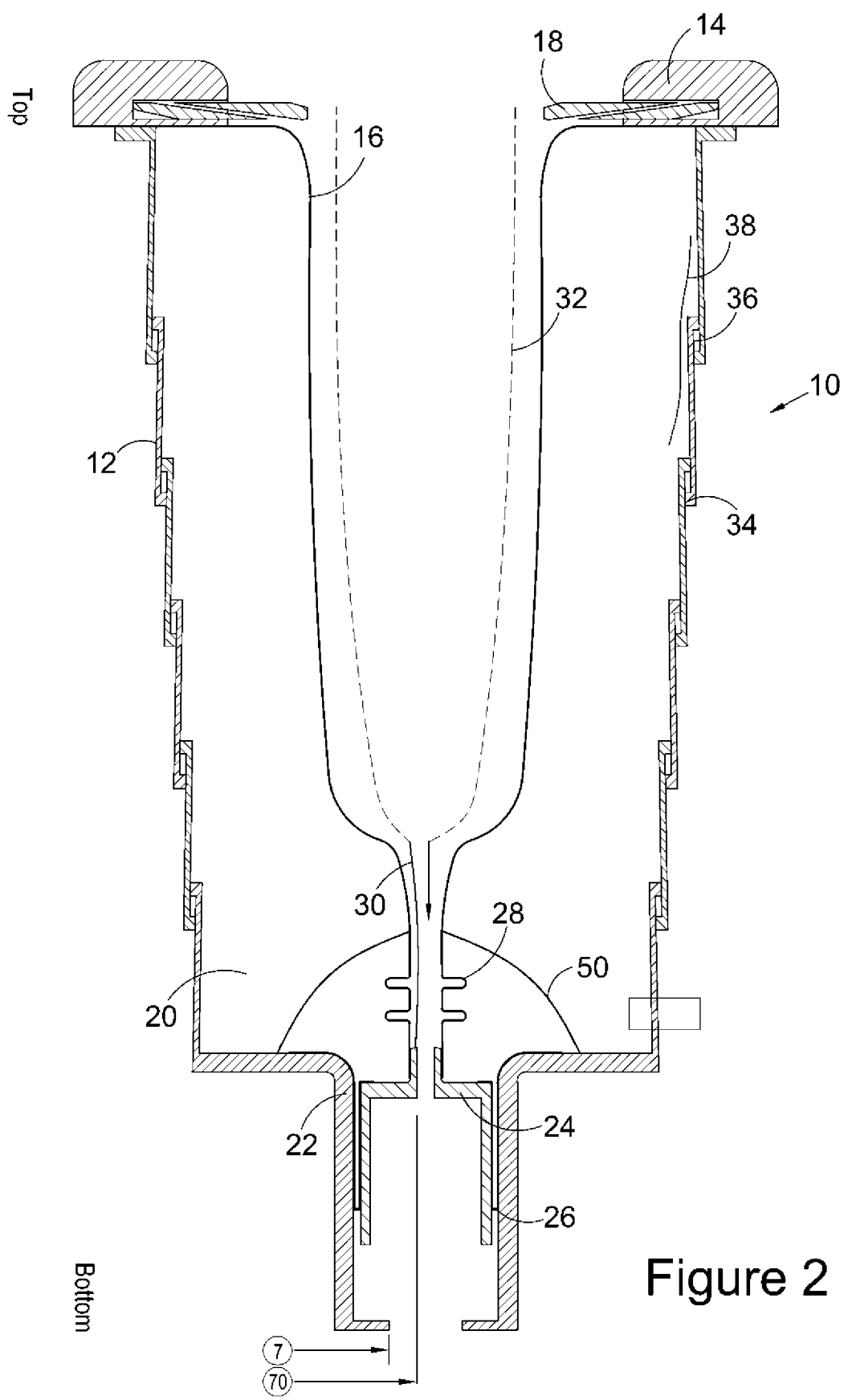
FIG. 2 is a cross-section through a prosthesis socket casting device.

When a socket is to be cast, typically an elastomeric liner is applied to the patient's residual limb. Attached to the end of the liner is a semi-rigid cable 30 that has a length that is adjustable externally of the casting device. The cable 30 is subsequently attached, tensioned and then externally locked to one end of the piston 24. The patient's liner clad stump 32 is then placed in the flexible membrane 16 and downward pressure is applied, as shown in FIG. 2. This causes movement of the flexible membrane 16 and the water to encase and support the patient's residuum and generally conform to its shape. Simultaneously with this, downward movement of the piston 14 is caused by engagement with the semi-rigid cable 30, thereby altering the distribution of the reactive fluid pressure applied to the patient's residuum. The incompressibility of the water causes a radial as well as an upward force to the stump, but also a downward force on the piston. In effect, the piston diameter reduces the net vertical upwards pressure on the distal stump. Consequently the remaining projected hydrostatic area (aperture area minus piston diameter area) is reduced, which increases the radial pressure. Hence, the stump is in a better position to be radially loaded. Use of the piston tends to cause more elongation of the stump and narrowing of the cast impression compared the situation that would arise in the absence of the piston.

Once the patient's full weight is applied an equilibrium position is reached. At this stage, the piston is at its most downward position and the volume of fluid in the cavity 20 is optimised. This primes the casting device. The patient's residuum 32 is then removed from the flexible membrane 16 so that a casting material can be applied to it. The semi-rigid cable 30 is subsequently re-attached to the liner. Once this is done, the patient's limb is re-inserted in the flexible membrane 16 and the piston 24 is pushed upwards. The cable 30 is subsequently tensioned and externally locked to one end of the piston 24. As noted above, once the patient's full weight is applied, the downward force on the piston reduces the net vertical upwards pressure on the distal residual limb, and consequently the remaining projected hydrostatic area (aperture area minus piston diameter area) is reduced, which increases the necessary radial pressure. Hence the stump is now in a better position to be radially loaded, will tend to cause elongation of the stump and narrowing of the cast impression. This improves the quality of the socket fit. Because the patient's weight determines how much downward force the piston can deliver as a function of its area, the casting device is automatically set.

Once the casting process has been completed, the user removes their residuum from the flexible membrane 16. To facilitate this, the external housing 12 is collapsible. More specifically, and as shown in FIG. 1 and, the housing 12 includes a plurality of interlocking cylinders 34 of gradually increasing diameter. These can be moved telescopically from an extended in use position to a collapsed position, in which it is relatively easy for the user to remove their residuum from the housing interior. To avoid leakage from the joints between adjacent cylinders, o-rings 36 may be provided. Alternatively or additionally, an inner liner 38 may be provided so that any fluid in the system is held between the flexible membrane 16 and the liner 38.

Figure 3:
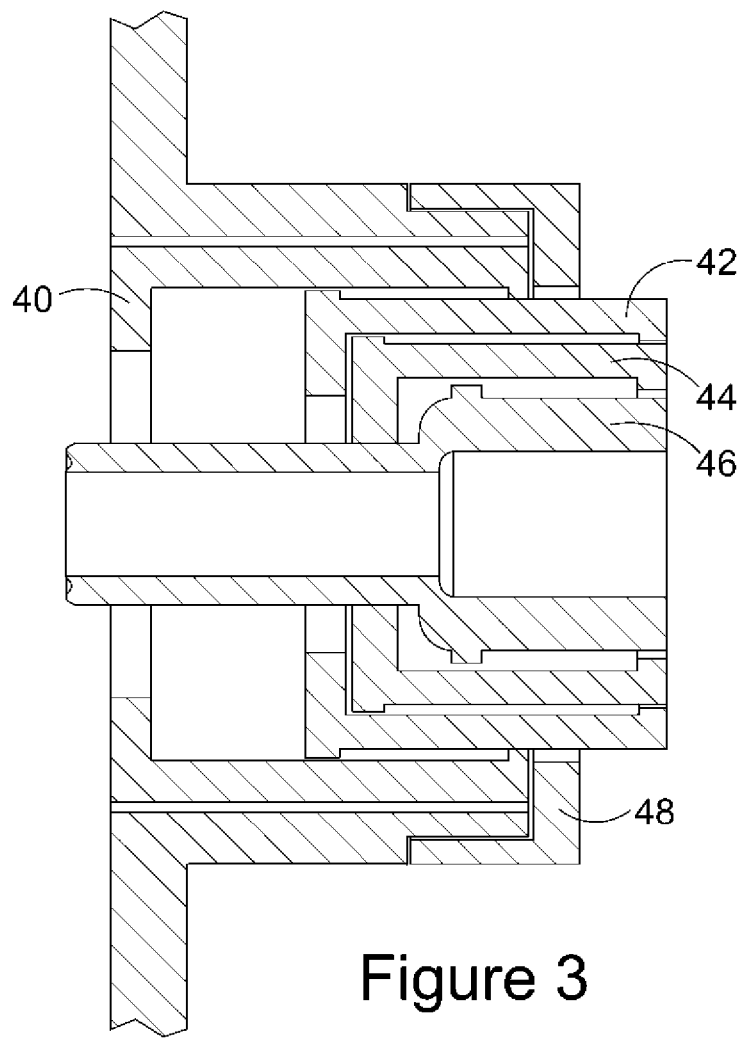
FIG. 3 is a cross-section through a variable size piston for use in the prosthesis casting device of FIGS. 1 and 2.

The effect of the piston of FIG. 1 varies depending on the surface area of the piston 24 in relation to the surface area of the stump 32 that is inserted into the flexible membrane 16. To take into account the fact that residual limbs 32 vary in diameter, a variable sized piston may be used. FIG. 3 shows an example of this. In this case, four selectively inter-lockable piston heads 40, 42, 44 and 46 are provided. Each has an annular surface for presenting to the interior of the housing. Surrounding the outer piston head 40 is a limiting ring 48 for limiting motion of that piston. Inner heads 42 and 44 each have a lip that co-operates with a lip on the adjacent larger head to limit its motion.

The annular surfaces of the piston heads co-operate to provide a range of different piston head surface areas. The interlocking piston heads can be selectively released from adjacent piston heads so that the effective surface area presented to the stump can be varied. When all four heads are interlocked the effective surface area is maximised. Releasing the inner head 42 from the outer head 40, decreases the area, and so. In use the piston head surface area would generally be selected depending on the weight of the patient.

Figure 4:
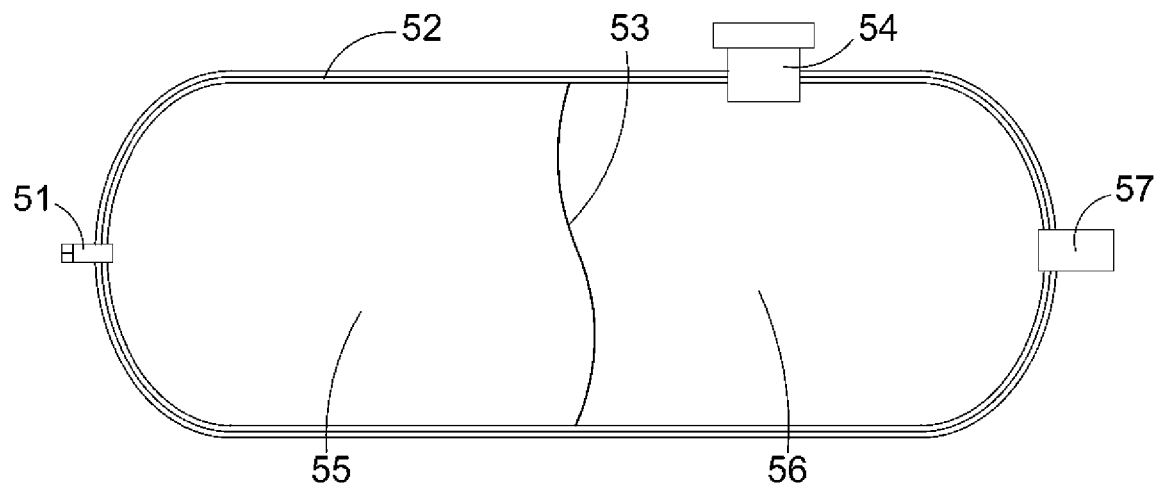
FIG. 4 is a cross-section through a pressurising tank for use with the devices of FIGS. 1 and 2.

In order to improve the quality of a casting, time is of the essence. To address this, the casting devices of FIGS. 1 and 2 can be adapted to co-operate with a pressurised fluid supply device. FIG. 4 shows an example of such a device. This has a main vessel 52 that is divided into an air chamber 55 and a fluid chamber 56 by a flexible membrane 53. Associated with the air chamber 55 is an air valve 51 for allowing pressurised air to be input. Associated with the fluid chamber 56 is a fluid filling point 54 for allowing water to be input and a fluid outlet 57 for connecting to a suitable inlet on the casting device (not shown). Within the fluid outlet 57 is a valve (not shown) that can be selectively opened/closed as and when desired.

In use, when the patient's residuum is in the casting device and the fluid volume is to be optimised, the fluid outlet 57 is connected to the casting device. Air is then input into the air chamber 55. This causes the flexible membrane 53 to expand and push against the fluid in the fluid chamber 57, thereby increasing the fluid pressure. Once a suitable pressure is reached, the fluid outlet valve is opened and fluid is allowed to flow rapidly into the cavity 20 of the casting device. Pressurising the fluid in this way allows quick filling of the main casting device and permits compensation for the volume variations of the individual residual limb. Once the fluid in the main casting device is optimised the valve within the fluid outlet 57 is closed creating a hydrostatic equilibrium induced by the patient's weight.

Figure 5:
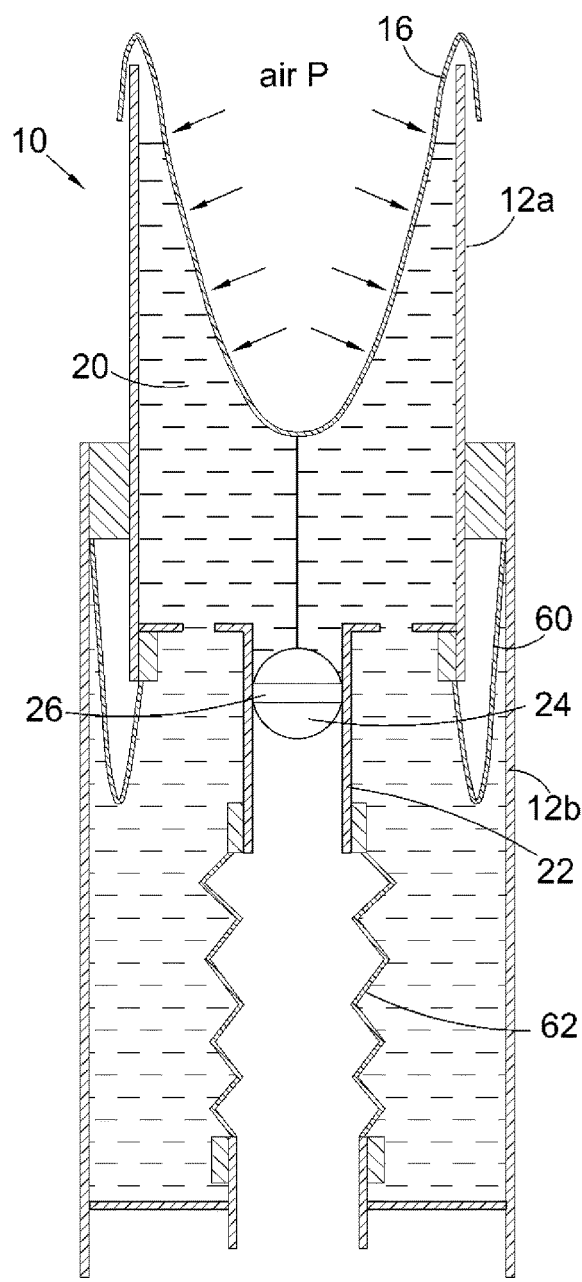
FIG. 5 is a cross-section through a prosthesis socket casting device.

FIG. 5 shows a prosthesis casting device 10 that has a rigid external housing 12 which comprises an upper section 12a and a lower section 12b. The upper section 12a and the lower section 12b of the housing are telescopic, with the upper section 12a at least partially fitting, preferably wholly fitting, within the lower section 12b in at least one configuration of the device 10. The upper section 12a and the lower section 12b are joined together by a seal 60, preferably a rolling membrane. The upper section 12a is generally positioned higher than the lower section 12b in use, such that the prosthesis casting device 10 is in an initial or pre-use configuration.

The flexible membrane 16 is coupled to the top of the upper section of the housing 12a. Opening into a lower end of the upper section 12a of the housing is a lower cup 22 within which is a moveable piston 24. A limiting mechanism (not shown) is provided to limit the downward piston movement. Between the piston 24 and the lower cup 22 is a rolling membrane 26 that extends fully around the periphery of the piston 24 and allows it to move whilst simultaneously providing a seal to prevent leakage of water from the cavity 20. A lower end of the flexible membrane 16 is attached to an upper end of the piston 24. The lower section of the lower cup 22 is sealed to the lower section 12b of the housing by a corrugated seal 62 or bellows.

There is a cavity 20 between the rigid external housing 12 and the flexible membrane 16. The cavity 20 is partially defined by both the upper section 12a and the lower section 12b of the housing. It is also partially defined by the flexible membrane 16, the seal 60, and the corrugated seal 62.

Figure 6:
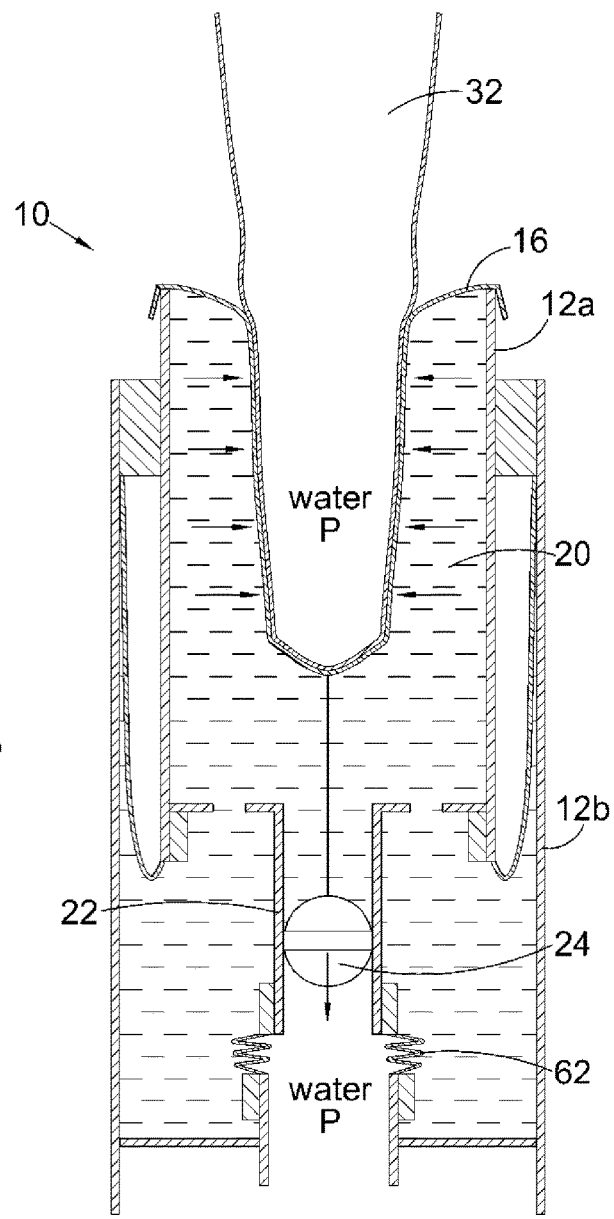
FIG. 6 is a cross-section through a prosthesis socket casting device.

FIG. 6 shows the prosthesis casting device 10 of FIG. 5 in a second, or in-use position. A patient's liner clad residual limb 32 has been pushed down into the flexible membrane 16. This has pushed the upper section 12a of the housing down into the lower section 12b of the housing, which has compressed the corrugated seal 62. The fixed volume of the water results in the water pressure P pushing the flexible membrane 16 against the patient's liner clad residual limb 32. The water pressure P also pushes the piston 24 down the lower cup 22.

Figure 7:
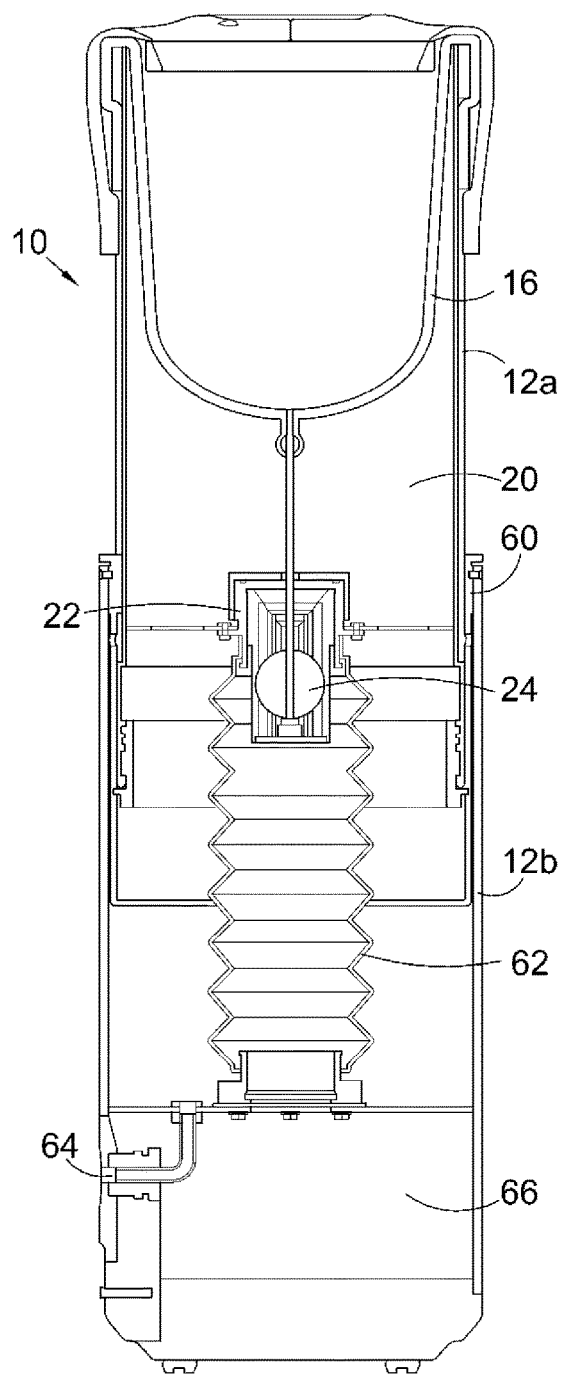
FIG. 7 is a cross-section through a prosthesis socket casting device.

FIG. 7 shows a prosthesis casting device 10 that has a rigid external housing 12 which comprises an upper section 12a and a lower section 12b. The upper section 12a and the lower section 12b of the housing are telescopic, with the upper section 12a at least partially fitting, preferably wholly fitting, within the lower section 12b in at least one configuration. The upper section 12a and the lower section 12b are joined together by a seal 60, preferably a rolling membrane. The upper section 12a is positioned higher than the lower section 12b, such that the prosthesis casting device 10 is in an initial or pre-use configuration.

The flexible membrane 16 is coupled to the top of the upper section of the housing 12a. Opening into a lower end of the upper section 12a of the housing is a lower cup 22 within which is a moveable piston 24. A limiting mechanism (not shown) is provided to limit the downward piston movement. Between the piston 24 and the lower cup 22 is a rolling membrane (not shown) that extends fully around the periphery of the piston 24 and allows it to move whilst simultaneously providing a seal to prevent leakage of water from the cavity 20. A lower end of the flexible membrane 16 is attached to an upper end of the piston 24. The lower section of the lower cup 22 is sealed to the lower section 12b of the housing by a corrugated seal 62.

There is a cavity 20 between the rigid external housing 12 and the flexible membrane 16. The cavity 20 is partially defined by both the upper section 12a and the lower section 12b of the housing. It is also partially defined by the flexible membrane 16, the seal 60, and a corrugated seal 62. There is a fluid outlet 64 which connects the cavity 20 to the outside of the prosthesis casting device 10 through the lower section 12b of the housing. This fluid outlet 64 can be used to add or remove fluid from the cavity 20. The lower cup 22 is contiguous with a second cavity 66, which is separate from the cavity 20.

Figure 8:
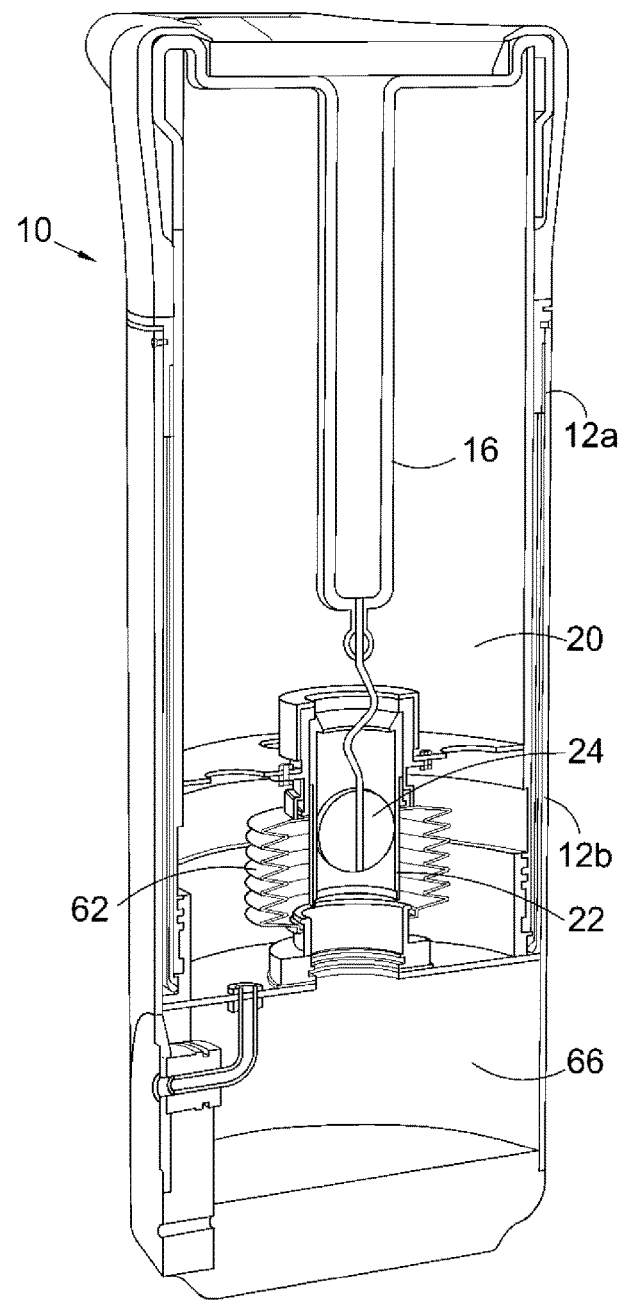
FIG. 8 is a perspective view of half a prosthesis socket casting device.

FIG. 8 shows the prosthesis casting device 10 of FIG. 7 in a second, or in-use configuration. The upper section 12a of the housing has been pushed down into the lower section 12b of the housing, which has compressed the corrugated seal 62. The fixed volume of the cavity 20 has resulted in the pressure of the fluid in the cavity 20 pushing the flexible membrane 16 in towards the centre of the upper section 12a. This pressure has also pushed the piston 24 down the lower cup 22.

As the piston 24 has moved closer to the bottom of the lower section 12b of the housing, the pressure in the second cavity 66 has increased. This increased pressure in the second cavity 66 results in an upwards force on the piston 24, which inhibits the downward movement of the piston 24.

Figure 9:
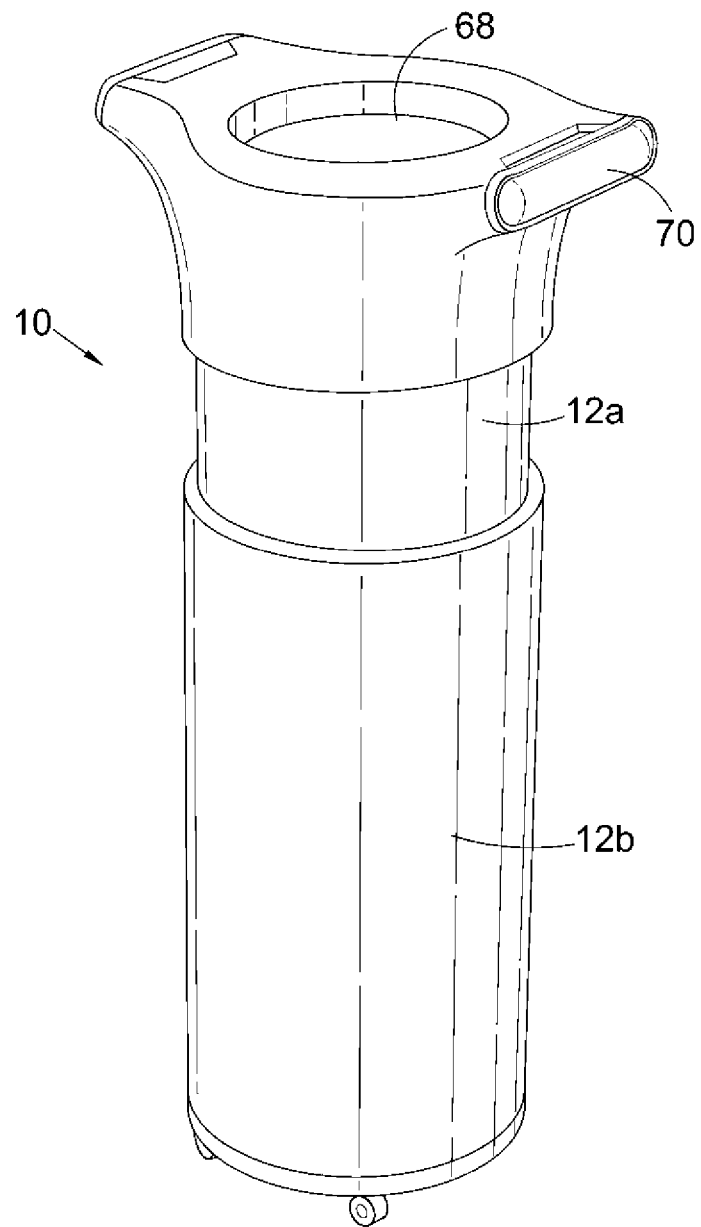
FIG. 9 is prosthesis socket casting device.

FIG. 9 shows a prosthesis casting device 10, with a rigid external housing comprising an upper section 12a and a lower section 12b. The upper end of the upper housing 12a comprises an opening 68, and handles 70. The handles 70 may be ergonomically designed handles.

FIGS. 10(a) to 10(c) show a method of using a prosthesis casting device 10. First, a patient's residual limb 32 is wrapped in plaster bandages. Then the patient's residual limb 32 is inserted into the prosthesis casting device 10 through the opening 68. The patient's residual limb 32 is pushed down into the prosthesis casting device 10, and pressure in the cavity 20 pushes the flexible membrane 16 against the patient's residual limb 32.

Figure 10:
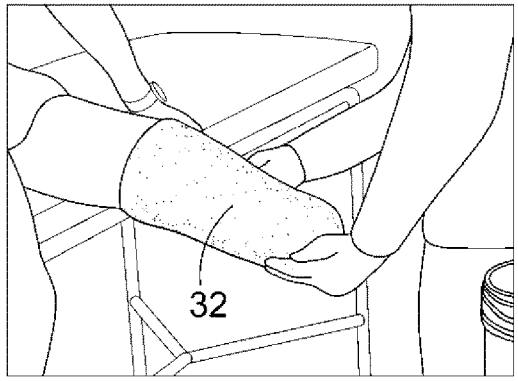
FIG. 10 (a) to (c) are a method of using a prosthesis socket casting device.
Figure 10:
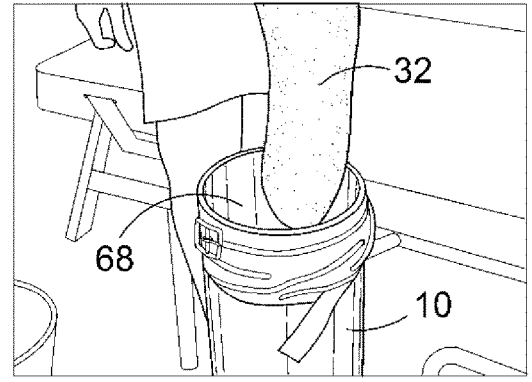
Figure 10:
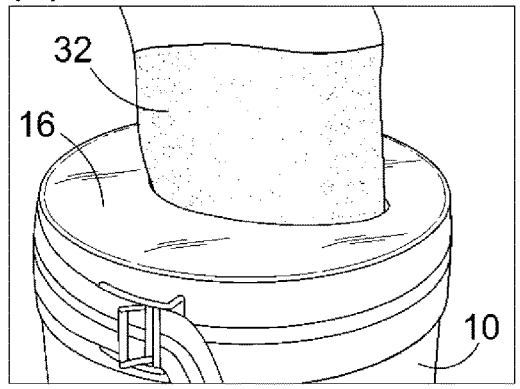
Figure 10:
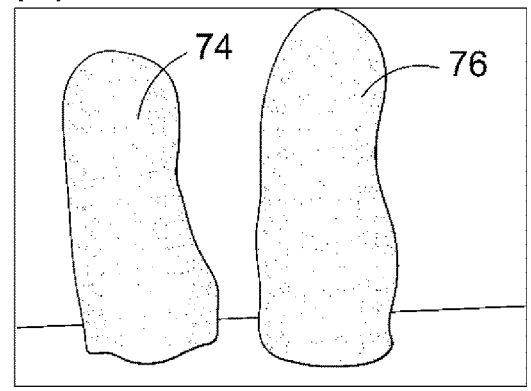
Figure 10:
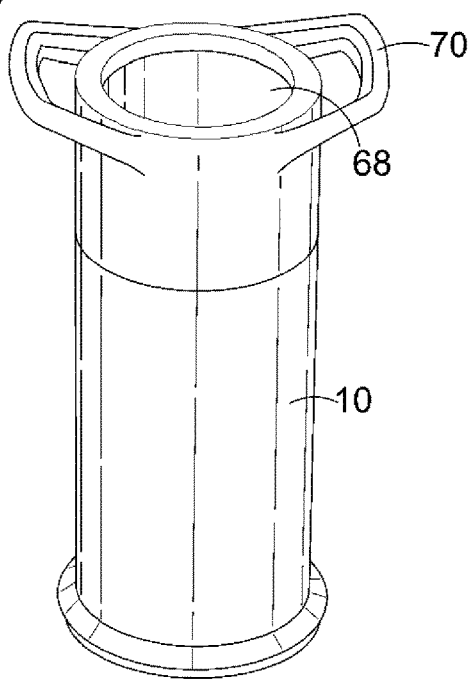
Figure 10:
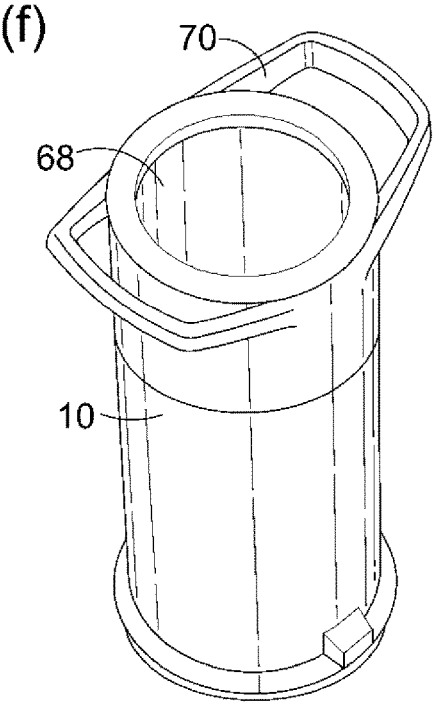

FIG. 10 (d) shows the negative mold 76 of the patient's residual limb 32, formed of the dried plaster in which the limb was wrapped, using the prosthesis casting device 10, and a second negative mold 74 of the patient's residual limb 32 made using a glass fibre bandage material. It will be appreciated that other suitable techniques and/or materials may be used to form the negative mold 76 and/or the second negative mold 74.

FIGS. 10 (*e*) and 10 (*f*) show different perspectives of a prosthesis casting device 10. The prosthesis casting device 10 comprises handles 70, preferably ergonomic handles, and an opening 68.

FIG. 10 (*g*) shows a method of using a prosthesis casting device 10. The method comprises a number of steps:
Step 1—apply plaster to a patient's residual limb 32
Step 2—position the prosthesis casting device 10 appropriately for the patient
Step 3—the patient inserts their residual limb 32 into the opening 68 of the prosthesis casting device 10
Step 4—the upper section 12*a* of the housing of the prosthesis casting device 10 is lowered into the lower section 12*b* of the housing until the water of the cavity 20 reaches the opening 68 of the upper section 12*a*
Step 5—the patient applies all their body weight to their residual limb 32, using a rack to aid balance
Step 6—the patient stands on their other leg
Step 7—the patient sits while the prosthesis casting device 10 is tilted slightly
Step 8—the upper section 12*a* is pushed further into the lower section 12*b* and the patient's residual limb is removed from the prosthesis casting device 10
Step 9—the plaster originally applied to the patient's residual limb 32 has set hard, and can be removed from the patient's residual limb 32

Figure 11:
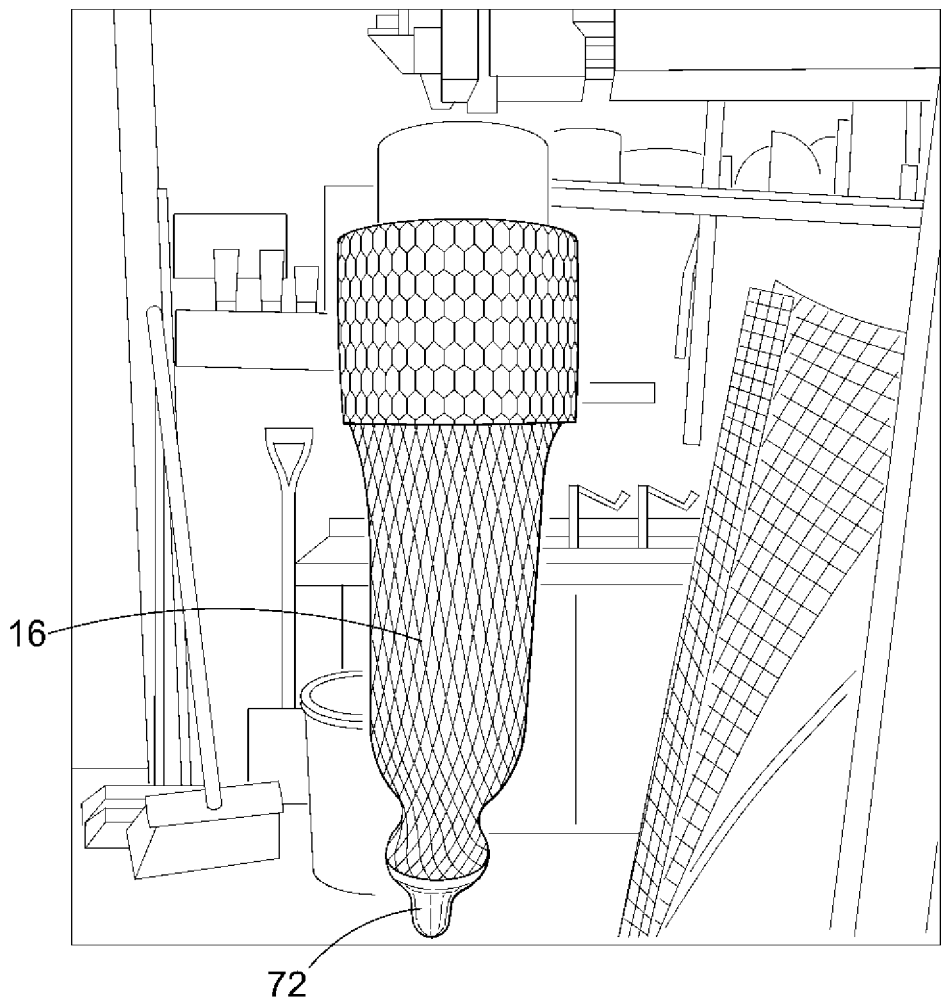
FIG. 11 is a flexible membrane for use with a method of using a prosthesis socket casting device.

FIG. 11 shows a flexible membrane 16 for use with a prosthesis casting device 10. The flexible membrane 16 comprises a weave such that the flexible membrane 16 constricts around the patient's residual limb 32 when pressure is applied along the limb 32, and the weave may preferably be a Chinese cuff weave, or similar. There is a connection point 72 at the bottom of the flexible membrane 16 for connecting the flexible membrane to a piston 24.

A skilled person will appreciate that variations of the disclosed arrangements are possible without departing from the invention. For example, a so-called Chinese cuff could be used in place of the piston arrangement described above. This allows the shape of the residuum to be captured, under a full loading condition, without the use of an elastomeric liner as well. This widens the clinical range of the casting device. In addition, as shown in FIGS. 1 and 2, a support web 50 optionally may be provided above the corrugated section 28 of the membrane 16 to reduce further any distortion caused by movement of the piston 24. Also, although the invention has been described primarily with reference to a movable piston, it will be appreciated that any means that are a function of the patient's weight could be used for altering the distribution of the reactive fluid pressure applied when the residual limb is received within the membrane. For example, the water pressure in the device generated by the patient's weight could be measured using pressure sensors and/or displacement transducers, and one or more actuators could be activated to pull on the distal stump end, the amount of pull being dependent on the measured water pressure and so the patient's weight. Accordingly, the above description of the specific embodiment is made by way of example only and not for purposes of limitation. It will be clear to the skilled person that minor modifications may be made without significant changes to the operation described.

The invention claimed is:

1. A prosthesis socket casting device having a housing, a flexible membrane depending from an upper end of the housing, the membrane being provided to receive a residual limb, the housing and the membrane defining a cavity for containing a fluid and means that are a function of a patient's weight for altering a distribution of the reactive fluid pressure applied when the residual limb is received within the membrane, wherein the housing comprises a telescoping housing.

2. A device as claimed in claim 1, wherein the altering means comprise a moveable piston at a lower end of the housing, and the piston is coupled to the housing with a rolling membrane.

3. A device as claimed in claim 1, wherein the altering means comprises a braided sleeve or member.

4. A device according to claim 3, wherein the braided sleeve or member is comprised or embedded in the membrane.

5. A device according to claim 1, wherein the housing comprises at least a first and a second section, wherein the first and second sections are movable relative to each other, such that at least part or all of the first section receivable within the second section.

6. A device according to claim 5, comprising a seal between the first and second sections.

7. A device according to claim 6, wherein the seal is or comprises a rolling membrane seal.

8. A device according to claim 1, comprising a longitudinal slide mechanism may be provided between an inner side surface of the second part of the housing and an outer side surface of the first part of the housing, the longitudinal slide mechanism being configured to only allow longitudinal movement of the first section relative to the second section, and by preventing rotational movement of the first section relative to the second section.

9. A device according to claim 1, wherein the cavity is a two part cavity, comprising at least a first cavity section and a second cavity section, wherein the first cavity section is provided within the first section of the housing and the second cavity section is at least partially defined by one or more or each of: an outer surface of the first section of the housing, an inner surface of the second cavity section and/or the seal; and at least one port or opening is provided between the first cavity section and the second cavity section to allow fluid communication there-through.

10. A device according to claim 1, wherein the altering means comprise a moveable piston at a lower end of the housing.

11. A device according to claim 2, wherein the piston is connected, coupled or attached to a liner that is applied or applicable to the patient's residual limb.

12. A prosthesis socket casting device as claimed in claim 1 that creates a hydrostatic balance between the patient's applied weight and reactive pressure in the casting device.

13. The prosthesis socket casting device according to claim 4, wherein the braided sleeve or member is comprised or embedded in a lower section of the membrane, and wherein the device comprises a diaphragm which comprises a braided material configured such that the diaphragm constricts or contracts around a patient's residuum when the residuum is pushed through an aperture in the diaphragm, and wherein the diaphragm comprises an upper section of the membrane.

14. A prosthesis socket casting device according to claim 1, wherein the housing has a variable volume, and the flexible membrane is movable responsive to variations in the volume of the housing.

15. A method of forming a cast of a residual limb, the method comprising using the prosthesis socket casting device according to claim 1, the method comprising:
- moving a membrane towards an inner surface of at least a first section of the housing by reducing the pressure in a first cavity section in the first section of the housing;
- providing a casting material onto a liner around a residual limb; and
- inserting the residual limb into a recess formed by the membrane.

16. A method according to claim 15, further comprising expanding or extending a housing of the prosthesis socket casting device by moving, sliding or telescoping at least part or all of at least part of a first section of the housing at least one of relative to, out of, or away from at least part of a second section of the housing in order to reduce the pressure in the first cavity.

17. A method according to claim 15, comprising applying a pressure above a threshold pressure to an altering means while the residual limb is inserted in the recess formed by the membrane, and then applying a force with the altering means to the membrane along the direction of the residual limb.

18. A method according to claim 17, comprising selecting the threshold pressure.

* * * * *